United States Patent [19]

Dietrich et al.

[11] Patent Number: 4,709,135
[45] Date of Patent: Nov. 24, 1987

[54] DEVICE TO HEAT INFUSION AND TRANSFUSION SOLUTIONS

[75] Inventors: Kurt Dietrich, Salach; Axel Stihler; Wolfgang Theilacker, both of Stuttgart, all of Fed. Rep. of Germany

[73] Assignee: Stihler Medizintechnik GmbH, Stuttgart, Fed. Rep. of Germany

[21] Appl. No.: 778,135

[22] Filed: Sep. 20, 1985

[30] Foreign Application Priority Data

Sep. 21, 1984 [DE] Fed. Rep. of Germany ....... 3434772

[51] Int. Cl.⁴ .................. H05B 1/02; A61M 5/14; F24H 1/12; B67D 5/62
[52] U.S. Cl. .................................. 219/303; 219/302; 219/308; 219/328; 604/114
[58] Field of Search ............... 219/296, 297, 298, 299, 219/301–305, 308, 309, 328–330; 165/46; 604/113, 114

[56] References Cited

U.S. PATENT DOCUMENTS

| 1,162,537 | 11/1915 | Yager | 219/304 X |
|---|---|---|---|
| 2,087,586 | 7/1937 | Tishman | 219/303 X |
| 2,576,558 | 11/1951 | Bede | 219/302 X |
| 2,657,097 | 10/1953 | New | 219/302 X |
| 2,673,919 | 3/1954 | Arvins et al. | 219/302 |
| 3,370,153 | 2/1968 | Du Fresne et al. | 165/46 X |
| 3,443,060 | 5/1969 | Smith | 219/302 |
| 3,551,641 | 12/1970 | Truhan | 165/46 X |
| 3,590,215 | 6/1971 | Anderson et al. | 219/308 X |
| 3,614,385 | 10/1971 | Horstmann | 219/303 |
| 3,629,552 | 12/1971 | Edging | 219/302 |
| 4,019,020 | 4/1977 | Bilbee | 219/298 X |
| 4,464,563 | 8/1984 | Jewett | 219/330 |

FOREIGN PATENT DOCUMENTS

| 0012123 | 11/1980 | European Pat. Off. |
|---|---|---|
| 1293954 | 4/1969 | Fed. Rep. of Germany . |
| 1954019 | 10/1970 | Fed. Rep. of Germany . |
| 1942162 | 3/1971 | Fed. Rep. of Germany . |
| 1953991 | 3/1971 | Fed. Rep. of Germany . |
| 2350264 | 4/1974 | Fed. Rep. of Germany . |
| 2515889 | 10/1976 | Fed. Rep. of Germany . |
| 2514376 | 10/1976 | Fed. Rep. of Germany . |
| 2619438 | 11/1977 | Fed. Rep. of Germany . |
| 2802993 | 7/1978 | Fed. Rep. of Germany . |
| 2833730 | 8/1980 | Fed. Rep. of Germany . |
| 3023416 | 1/1981 | Fed. Rep. of Germany . |
| 3217471 | 11/1982 | Fed. Rep. of Germany . |
| 1446412 | 8/1976 | United Kingdom . |
| 1578015 | 10/1981 | United Kingdom . |

OTHER PUBLICATIONS

Pamphlet "BT 794: Trocken-Blut/Flüssigkeits--Wärmer", from DIDECO GmbH, D-8027 Neuried--Müchen, Federal Republic of Germany.
Der Chirurg, 23, 1952, 1, p. 47—Dr. med. Günter Maurer, "Regulierebare Heizvorrichtung für Intravenose Dauertropinfusionen".

Primary Examiner—Anthony Bartis
Attorney, Agent, or Firm—John F. Witherspoon

[57] ABSTRACT

A device for heating infusion and transfusion solutions includes an automatically temperature controlled, electrically heated heat exchange unit having an exposed cylindrical outer surface provided with a helical groove removably receiving and holding with a clamping effect a flexible infusion tube through which the solution to be heated flows. A sleeve of thermal insulation material having its inner surface covered with an aluminum foil closely surrounds the outer surface of the unit and the tube seated in the groove. Safety clamps secured to casing portions at opposite ends of the heat exchange unit insure that the tube is held in the groove.

4 Claims, 3 Drawing Figures

DEVICE TO HEAT INFUSION AND TRANSFUSION SOLUTIONS

The invention relates to a device to heat infusion and transfusion solutions, whereby a heat exchange cylinder, raised to a specific temperature by means of heating elements and automatic controllers, comprising a groove running helically on the outside in which a tube is disposed and through which the infusion of transfusion solution is led, are provided.

Such a device is known in the art (prospectus of the DIDECO corporation s.P.a.). In this respect an approximately 4 m long tube is laid into the helical groove formed in the outside surface of the heating cylinder. The disadvantage of this arrangement lies in the fact that it makes a certain length of tubing a pre-requisite such that the normal set of transfusion and infusion instruments or the tube that belongs to this set of instruments and that is shorter cannot be used. The length, however, of approximately 4 m in the known device in the art is necessary in order to reach the desired blood temperature. The tubes that are commonly used for infusions and that are components of the normal set of instruments are only approximately 190 cm long. Thus they are incompatible with the known device in the art. Furthermore, there is also the risk of heating the blood nonuniformly since the blood that flows on the inside of the tube, which has direct contact with the heat exchange cylinder, will eventually heat up more than the blood that flows in the tube along its outside, along which the tube has direct contact with the atmospheric environment.

In addition to this, devices are known in the art in which the tube carrying the infusion or transfusion fluid passes through an intake reservoir that is placed between two warming plates (DE-OS No. 28 02 993, DE-OS No. 30 23 416, De-OS No. 19 54 019, European patent disclosure No. 0 012 123). The disadvantage of these arrangements lies in the fact that two serial sets of infusion instruments cannot be used. Moreover, there is also the disadvantage that the process of guiding the blood through this intake reservoir after it has bowed out (which is necessary for uniform heating) will show such a high degree of drag that it is possible that the remaining blood taken from the blood bank will no longer flow through. The loss of pressure in the apparatus is high. Rapid infusions are no longer possible with this apparatus.

Heating the infusion or transfusion liquid in a corresponding apparatus by means of an exothermic chemical reaction (DE-OS No. 25 15 889) is also known in the art. Here, too, the use of serial sets of instruments is not possible; furthermore, the quantity of heat emitted from an exothermic chemical reaction can be controlled only with difficulty.

Other devices are known in the art in which the transfusion or infusion solution is led through a water bath. In devices of this nature (U.S. Pat. No. 3,629,552) the tube is wound with more than twenty turns helically on a support frame formed by two U-shaped struts, and together they are submerged into a steel canister, containing a liquid that is continuously heated. In another apparatus (U.S. Pat. No. 3,614,385) an electric heater is attached beneath a chimney-like convection tube. By this means a convection current is obtained in the tank. In addition to the chimney-like convection tube, there is also the coiled tubing, wound helically with approximately ten turns through which the transfusion or infusion solution is led. This arrangement is also inordinately complicated. The use of serial sets of instruments is not possible.

In the foreground of efforts for a device to heat infusion and transfusion solutions there is in addition to the fact that the infusions and transfusions, especially blood, are to be primarily heated, the requirement that the heater used be adjustable to a specific value. Thus the controllability of the heater is closely related to the construction of the heater itself, since the technical purpose is defined in terms of the latter in order to be able to fill specific demands for precision of control, but in particular, also for reliability of control.

Whereas on the one hand one avoids cold shocks by heating an infusion or transfusion, as for example (during emergency care after an accident) a cold shock can trivially occur if the patient gets too cold, on the other hand one must guarantee with absolute certainty that the infusion or transfusion will not be raised to more than 39.5° since at higher temperatures there is the risk that they blood will coagulate. In this respect one of the known devices in the art (EP No. 0 012 123), mentioned above, provides that the transfusion or infusion solution is converted from low flow velocities to a specific rate of flow. This solution is also inordinately complicated.

Therefore, the purpose of the invention is to create a device of the type mentioned in the beginning, which is considerably simpler than known devices in the art. In particular, the purpose is to be able to use the usual set of infusion instruments attainable on the market, thus wholly "normal" sets of infusion instruments. They usually comprise a tube length of 1.9 m. The purpose also includes that one no longer needs an intake reservoir or some such similar thing. No tubes or guidelines, specially designed for the heating apparatus, should be necessary. Furthermore, it is clear that each solution must be appropriate to this task in order to guarantee with absolute certainty a shut-off when exceeding a temperature of 39.5° C.

This invention solves this problem through the fact that the heat exchange cylinder is enclosed externally in a heat-insulating sleeve.

By means of the heat-insulating sleeve, which is pressed against the fluid conduit which projects somewhat beyond the surface of the heat exchange cylinder 3, and which is provided on the inside surface thereof preferably with aluminum foil 11; radiation of heat energy from the tube into the atmospheric environment has been substantially completely avoided. Furthermore, uniform heating of all areas of the tube is guaranteed. Thus it is necessary to make due with two or three contacts of a cylinder that has preferably a diameter of 10 to 15 cm. Thus normal serial sets of infusion instruments can be used. The use of such a device simplifies handling, lowers costs and solves a large number of problems mentioned above. Also, no additional aids (as for example when submerging tubing in water tanks) are necessary. Since the loss of pressure through special intake reservoirs or especially long lines is avoided, the device can also be used together with infusion pumps. An infusion or transfusion solution runs through the tube without leaving a residue. In the same manner the device can also be used to heat rinse solutions during surgical operations. Furthermore, its simple and fast readiness for service must be stressed, which is a given not only in the operating room but also at the ambulance, the intensive care ward, dialysis ward, and all nursing wards such as in rescue services (ambulance and rescue helicopter). In particular, rescue services show a simple possibility of providing thoroughly cold accident patients with infusions or transfusions at the site of the accident and during transport. The small compact construction must be stressed here and the low consumption of electricity, which makes it possible to supply electricity by means of 12 V systems of a vehicle or its batteries.

An embodiment of the invention and its other advantageous forms will be described in the following with the aid of the accompanying drawings in which FIG. 1 illustrates one embodiment of the invention;

Figure 1:
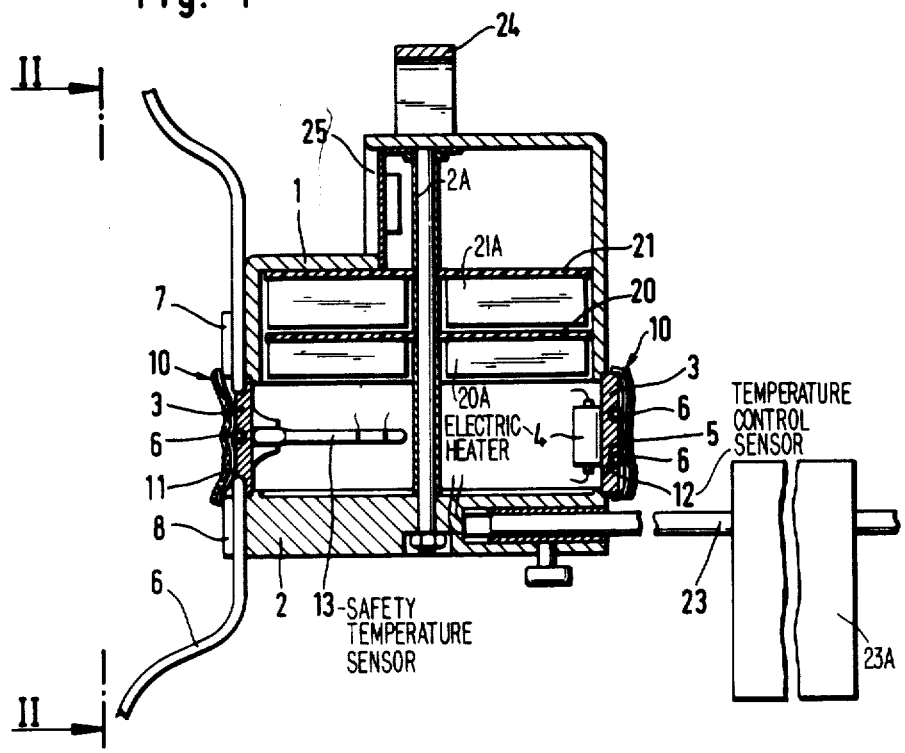
Figure 2:
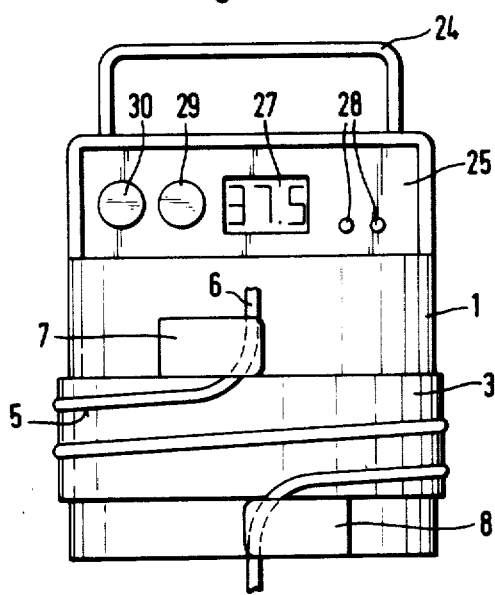
FIG. 2 is a side elevational view of the device shown in FIG. 1.
Figure 3:
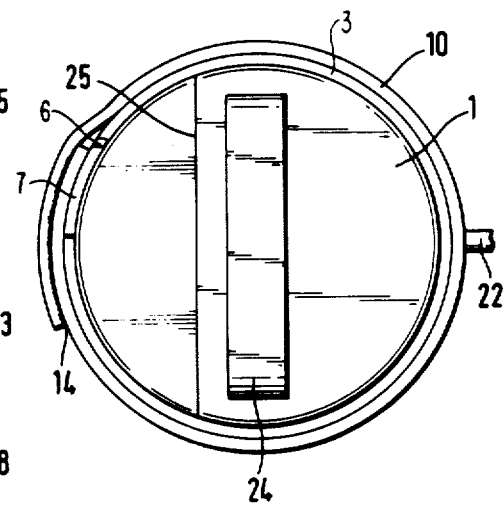
FIG. 3 is a top plan view of the device shown in FIG. 1 with the thermal insulation cover removed.

The device, shown in FIGS. 1-3, shows a cylindrical casing that is fastened to the top of a base 2. A heat exchange cylinder 3 is held between the casing 1 and the base 2 by a screw 2A. It is heated by electrical heaters 4 secured to the inside surface of cylinder 3. There is a groove 5 around the exterior surface of the heat exchange cylinder 3. Groove 5 runs helically around the cylinder 3, with inlet and outlet grooves. The tube 6, which conducts the fluid to be heated, is a component of the usual commercial set of infusion equipment, is approximately 190 cm. long, and is disposed in the groove 5. To ensure that the tube 6 is disposed and held in the groove 5, there is at the bottom of the groove entrance safety clamp 7 and at the top end of the groove an exit safety clamp 8. Clamps 7 and 8 hold the tube 6 so that it cannot be removed without applying a certain amount of force. The heat exchange cylinder 3 is preferably made of aluminum with an external diameter of 13 cm. and a height of 4 cm. In order to improve and guarantee thermal transfer, the tube 6 forms a positive connection in the groove 5 through a specific clamping effect. In the example of the embodiment the groove 5 is 3 mm. deep and has a radius of 2 mm. at its base so that the tube 6 has as much surface contact as possible for thermal transfer. Usually the tube also has a radius of 2 mm., and an external diameter of 4 mm. Thus it projects a little above the exterior surface of the heat exchange cylinder 3. In order to attain a clamping effect, the groove 5 is somewhat cut back, thus at its opening it is only 3.7 or 3.8 mm. wide in the external surface of the heat exchange cylinder, whereas its largest internal diameter is 4 mm.

To protect against thermal radiation, the heat exchange cylinder 3—with the inlaid tube 6—is enclosed in a thermal-insulating sleeve 10. The sleeve is flexible, preferably made of textile materials or corresponding synthetic weaves. After laying the tube 6 into the groove 5, the sleeve 10 is attached to the exterior surface of the heat exchange cylinder 3. For this purpose it has a clinging fastener 14.

The insulating sleeve 10 is lined internally with aluminum foil 11 that is pleated which helps prevent heat loss and facilitates the transfer of heat from the heat exchange cylinder 3 to that part of the tube 6 that is not in direct contact with the groove 5 (that part of the tube 6 that projects approximately 1 mm. above the surface of the heat exchange cylinder 3). This insures that the tube 6 will be heated evenly and uniformly to a specific temperature.

A temperature sensor 12 is located near each heating element 4. The temperature sensor 12 conveys the input measuring variable for the heat regulating units.

Furthermore, a mercury thermometer 13, which makes contact between two electrical contacts upon reaching a specific temperature, is attached to the inner perimeter of the heat exchange cylinder. Its function is to guarantee a shut-off when the pre-set temperature is exceeded. In order to check this function, another heater that can be actuated externally, and thus separately, is built into the base of the mercury thermometer with which it is fastened on the inside of the heat exchange cylinder. If this heater is actuated, for example via a test button, the shut-off must take place and be recorded as a disturbance.

The boards 20 and 21 supporting the components of the electric circuit 20A, 21A are secured in the casing 1. Support tube 23 extends from suspension apparatus 23A which contains a transformer which provides a 12 V current to the heaters. When assembled the entire device can be hung from a stand next to the patient's bed or fastened next to the stretcher in an ambulance. A handle 24 is attached to the top of the casing 1. The operating and indicating panel 25 has a digital temperature indicator 27, two lights 28, to show when the heater element is on. Two control buttons 29, 30 for starting and stopping are also located on the panel 25.

What is claimed is:

1. In a device for heating infusion and transfusion solutions that includes a heat exchange unit, means for electrically heating said unit and means for automatically controlling the temperature of said unit, the improvement which comprises:

(a) said heat exchange unit having a cylindrical outer surface with a groove running helically around said outer surface, said groove being cut into said outer surface so that the interior contour and dimensions of the groove will removably hold a tube with a clamping effect, (b) a flexible infusion tube seated in said groove through which said infusion or transfusion solution is adapted to flow, (c) a sheet of heat-insulating material in the form of a sleeve surrounding said outer surface, said sleeve being pressed in close proximity to the surface portion of said tube that projects above the grooves in said exterior surface of said heat exchange cylinder, and (d) an insertion safety clamp at a first terminal of said groove and an exit safety clamp at a second terminal of said groove, said clamps being both formed of small plates partially covering said groove, said plates being secured adjacent to said groove on a surface of first and second casing portions, said casing portions being arranged on opposite end faces of said heat exchange unit, said casing portions holding said heat exchange unit therebetween with said cylindrical outer surface exposed.

2. A device as defined in claim 1 in which an inside surface of said sleeve is covered with an aluminum foil, and said aluminum foil is in contact with said cylindrical outer surface.

3. A device as defined in claim 1 in which said groove runs with one and a half to two and a half helical turns.

4. A device as defined in claim 1 in which said tube has an external diameter of about 4 mm, said heat exchange cylinder has an external diameter of about 100 to about 150 mm, said groove having a radius of curvature of about 2 mm at its base, and said groove being about 3 mm deep.

* * * * *

UNITED STATES PATENT AND TRADEMARK OFFICE
CERTIFICATE OF CORRECTION

PATENT NO. : 4,709,135

DATED : November 24, 1987

INVENTOR(S) : Kurt Dietrich, Axel Stihler and Wolfgang Theilacker

It is certified that error appears in the above-identified patent and that said Letters Patent is hereby corrected as shown below:

Column 2, line 46, after "the", first occurrence, insert --outside--.

Signed and Sealed this

Fifth Day of July, 1988

Attest:

DONALD J. QUIGG

Attesting Officer

Commissioner of Patents and Trademarks